(12) United States Patent
Lim

(10) Patent No.: US 11,071,766 B2
(45) Date of Patent: Jul. 27, 2021

(54) STRAWBERRY PLANT EXTRACT AND USE THEREOF

(71) Applicant: RIWAY (SINGAPORE) PTE. LTD., Singapore (SG)

(72) Inventor: Boon Hong Lim, Singapore (SG)

(73) Assignee: RIWAY (SINGAPORE) PTE. LTD., Singapore (SG)

( * ) Notice: Subject to any disclaimer, the term of this patent is extended or adjusted under 35 U.S.C. 154(b) by 174 days.

(21) Appl. No.: 16/403,501

(22) Filed: May 4, 2019

(65) Prior Publication Data
US 2019/0336556 A1     Nov. 7, 2019

Related U.S. Application Data

(60) Provisional application No. 62/667,651, filed on May 7, 2018.

(51) Int. Cl.
| | | |
|---|---|---|
| *A61K 36/73* | (2006.01) | |
| *A61K 31/7004* | (2006.01) | |
| *A23L 33/105* | (2016.01) | |

(52) U.S. Cl.
CPC ............ *A61K 36/73* (2013.01); *A23L 33/105* (2016.08); *A61K 31/7004* (2013.01); *A23V 2002/00* (2013.01); *A23V 2200/30* (2013.01); *A23V 2250/21* (2013.01); *A61K 2236/33* (2013.01)

(58) Field of Classification Search
CPC ............... A61K 36/73; A61K 31/7004; A23V 2250/21; A23L 33/105
See application file for complete search history.

(56) References Cited

U.S. PATENT DOCUMENTS

| | | | | |
|---|---|---|---|---|
| 2013/0115322 A1* | 5/2013 | Stoner | ............... | A23L 33/105 424/765 |
| 2017/0360861 A1* | 12/2017 | Humphreys | ......... | A61K 36/185 |

FOREIGN PATENT DOCUMENTS

JP      5107103 B2 * 12/2012

OTHER PUBLICATIONS

Froney et al., The Composition of Strawberry Aroma is Influenced by Cultivar, Maturity, and Storage, vol. 35(6), Oct. 2000 (Year: 2000).*
Rollitup.org (https://www.rollitup.org/t/48-hours-of-darkness-before-harvest.561431/), Sep. 10, 2012 (Year: 2012).*
Gasparrini, M. et al., Anti-inflammatory effect of strawberry extract against LPS-induced stress in RAW 264.7 macrophages, Food and Chemical Toxicology, 2017.
Kim, D.S. et al., Composition of Secondary Metabolites in Various Parts of 'Seolhyang' Strawberry Plants, Kor. J. Hort. Sci. Technol., 31(2):224-230, 2013.
Molinett, S. et al., Chilean Strawberry Consumption Protects against LPS-Induced Liver Injury by Anti-Inflammatory and Antioxidant Capability in Sprague-Dawley Rats, Evidence-Based Complementary and Alternative Medicine, 2015.

* cited by examiner

*Primary Examiner* — Terry A McKelvey
*Assistant Examiner* — Jacob A Boeckelman

(57) ABSTRACT

A strawberry plant extract, an extraction method and a novel use thereof are disclosed. The extraction method comprises: darkly incubating a strawberry plant between the anthesis stage and the first harvest stage, harvesting the strawberry plant with the green-white, white or white-red color of the strawberry fruit, and extracting the strawberry plant with ethanol to obtain the strawberry plant extract. The invention further relates to the use of a strawberry plant extract for the manufacture of a composition, wherein the composition is for inhibiting the secretion of cell promoting inflammatory mediators.

10 Claims, 11 Drawing Sheets

STRAWBERRY PLANT EXTRACT AND USE THEREOF

RELATED APPLICATIONS

The application claims the benefit of priority to U.S. provisional application No. 62/667,651, filed on May 7, 2018, of which is incorporated herein by reference in its entirety.

FIELD OF THE INVENTION

The present invention relates to a strawberry plant extract and the use thereof; in particular to a strawberry plant extract which contains a phytochemical compound available to bind to the inhibitory region of NF-κB protein for immunomodulation and anti-inflammatory.

BACKGROUND OF THE INVENTION

Conventional phytochemical are chemical compounds produced by plants so as to be beneficial to human health and are extracted and purified so as to applicable for food or medical products.

The phytochemical category includes compounds recognized as essential nutrients, which are naturally contained in plants and are required for normal physiological functions, so must be obtained from the diet in humans.

Nuclear factor kappa-light-chain-enhancer of activated B cells (NF-κB) is a protein complex that controls the transcriptional work of DNA in biological cells. Its existence is found in all animal cells. The work to deal with such as stress, cytokines, free radicals, UV radiation, oxidized low-density protein, bacteria or virus antigens and other factors on the cells to stimulate, and regulate the body's immune system. Abnormal regulation of NF-κB is associated with cancer, inflammation, autoimmune diseases, sepsis, and viral infections.

Therefore, NF-κB can be used as a selective marker to improve a variety of inflammatory diseases, including arthritis, asthma and autoimmune diseases, in the past medical research reports, mostly in the way of drug synthesis to find can interfere with NF-κB regulatory pathway compounds.

The present invention has arisen to mitigate and/or obviate the afore-described disadvantages.

SUMMARY OF THE INVENTION

Accordingly, one aspect of the present invention provides a method of extracting a strawberry plant extract which promotes the performance of a phytochemical compound by controlling plant growth environment conditions.

To obtain the above aspect, a method for extracting a strawberry plant extract comprises following steps is provided: performing a darkly incubation of a strawberry plant between anthesis stage and first harvest stage; harvesting the strawberry plant in a green-white, white or white-red color of the strawberry fruit; and extracting the strawberry plant with ethanol to obtain the strawberry plant extract.

According to an embodiment of the present embodiment, roots, stems, leaves, calyx, and 5%-40% of strawberry fruits.

According to one embodiment of the present embodiment, wherein the ethanol is 95% ethanol.

According to an embodiment of the present embodiment, wherein the strawberry plant is selected from the group consisting of *Fragaria* x *ananass, Fragaria havatai* Makino, *Fragaria chiloensis, Fragaria nilgerrensis, Fragaria nipponica, Fragaria nilgerrensis* Schlecht., *Fragaria virginiana, Fragaria* x *vesca, Fragaria iturupensis* Staud and a group consisting of any combination.

According to an embodiment of the present invention, the strawberry plant extract comprises a Compound (A) which available to bind to a region of inhibition of NF-κB:

Compound (A)

Another aspect of the present invention is to provide strawberry plant extract for the manufacture of a composition for inhibiting secretion of cell-promoting inflammatory mediators.

According to one embodiment of the invention, a composition comprising a strawberry plant extract and an optional edible carrier is provided.

According to an embodiment of the present embodiment, the food composition is any one of food supplement, nutritional supplement and special nutritious food.

According to an embodiment of the present invention, wherein the food composition is any one of beverage, pastilles, pills, capsules, lozenges, granules, powders, suspensions, sachets, pastilles, confectionery, sticks, and syrups.

DETAILED DESCRIPTION

Phytochemicals according to a preferred embodiment of the present invention are selected from database of plant compounds by way of computer-aided drug design and bind with a NF-κB inhibition zone, and the phytochemicals are employed to produce medical products, food supplements or nutritional supplements in an extraction manner. Preferably, the medical products, food or nutritional supplements enhance immune regulation and anti-inflammatory.

Experimental Example 1-1: Screening System Construction

The selecting system is established based on a natural product index approach (NPIA) so as to select the phytochemicals. For example, selecting one of 6000 training groups, and the one training group is tested by using Fischer's Cross-Validation so as to confirm its confidence level.

Figure 1:
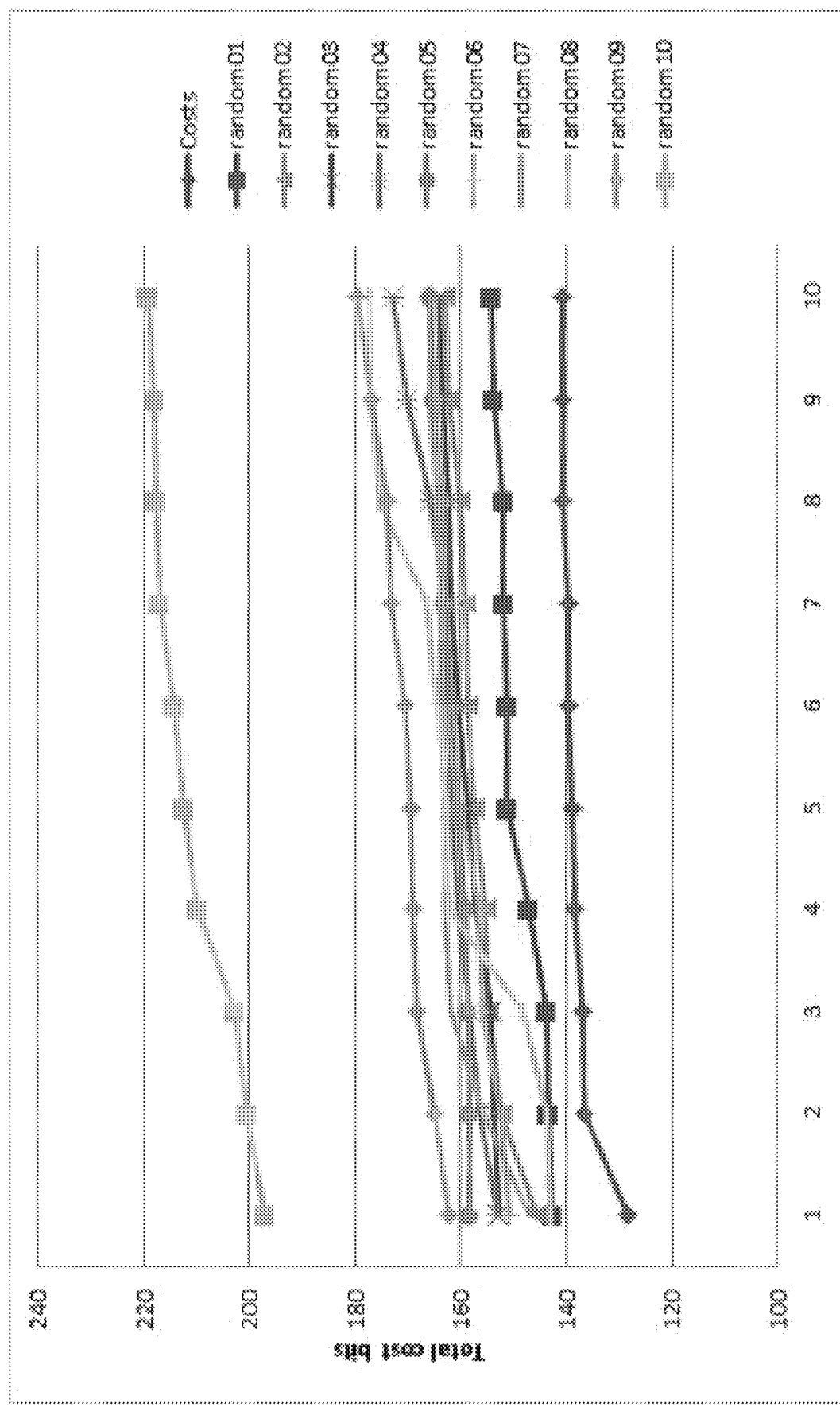
FIG. 1 is a schematic view illustrating a testing result by using Fischer's Cross-Validation according to a preferred embodiment of the present invention.

In a test, a molecular structure of the training group is randomly distributed to an active organism efficacy group and is executed for ninety-nine times, such that a tester observes whether the efficacy group randomly reorganized is identical to data of a cost group. With reference to FIG. 1, in the test, the molecular structure is executed for ninety-nine times by using Fischer's Cross-Validation, wherein a result of last ten of the ninety-nine times is not identical to the data of the cost group by using random 01 to random 10, hence the one training group has a high confidence level and is not produced randomly.

Thereafter, the efficacy group is used as stacking conditions, wherein three-dimensional configuration of compound of the one training group is chemically stacked through the efficacy group in a three-dimensional space, and Gasteiger-Hitckel charge is added to the compound of the one training group, then Chemistry at Harvard Macromolecular Mechanics (CHARMM) force field is applied to the compound of the one training group, wherein $sp^3$-hybridized carbon atom is used as a probe so as to calculate contour information of NF-kB in the three-dimensional space.

Figure 2:
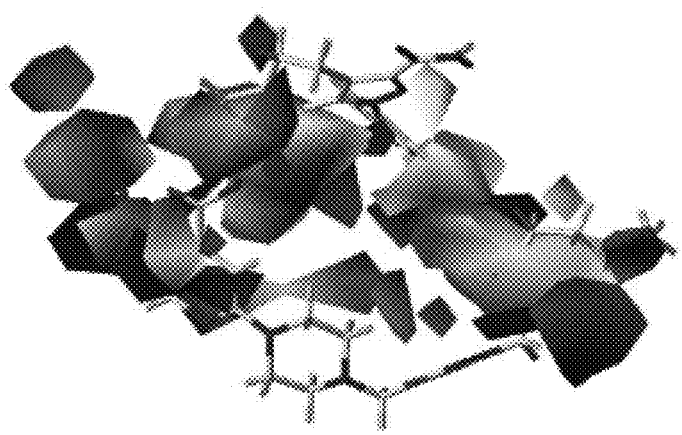
FIG. 2 is a schematic view illustrating the contour information of NF-kB in the three-dimensional space according to the preferred embodiment of the present invention.

FIG. 2 is a schematic view illustrating the contour information of NF-kB in the three-dimensional space, wherein $r^2_{ncv}$ coefficient is 0.99 after calculation, a standard error of estimate (SEE) is 0.16, the contour information of NF-kB contains steric, electrostatic, hydrophobic, hydrogen donor, and hydrogen acceptor, wherein the steric is 0.16, the electrostatic is 0.18, the hydrophobic is 0.20, the hydrogen donor is 0.21, and the hydrogen acceptor is 0.25.

Experimental Example 1-2: Plant Compound Exploration

The phytochemicals in the database of the plant compounds are produced in the three-dimensional configuration, and the phytochemicals are stacked on the efficacy group, then stacked three-dimensional configurations of the phytochemicals are recorded. Thereafter, biological activities of the stacked phytochemicals are predicted with chemical outline so as to obtain the formula (1), the formula (2), the formula (3), the formula (4), and the formula (5), wherein the formula (1) is

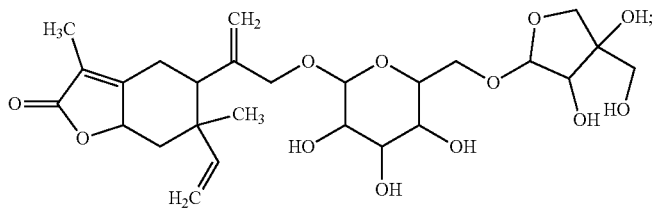

the formula (2) is

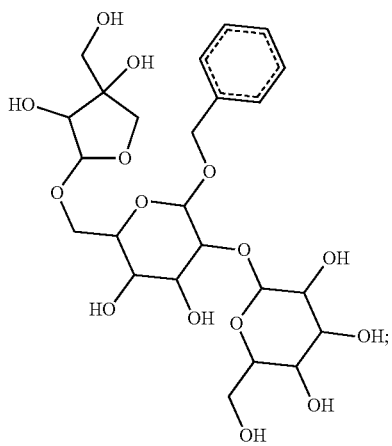

the formula (3) is

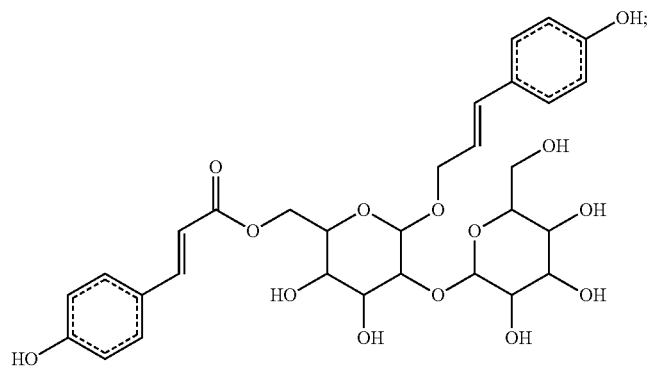

the formula (4) is

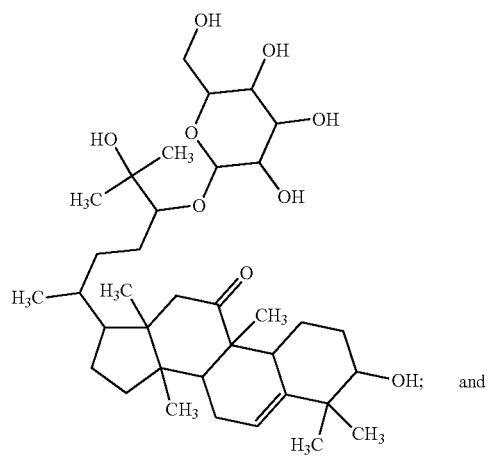

and the formula (5) is

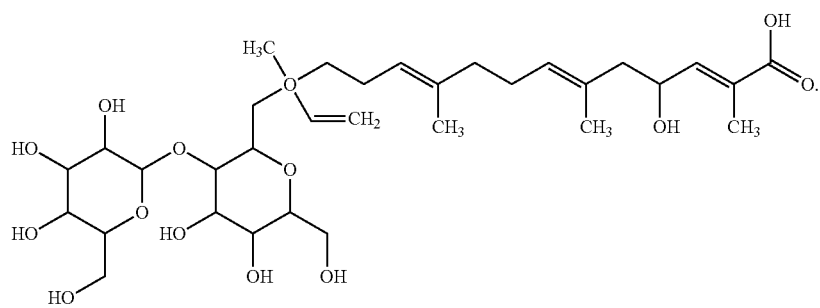

wherein the plant compounds are selected from strawberry, *Pyrus bourgaeana*, *Boschniakia rossica*, *Siraitia grosvenorii*, sweet pepper fruits of *Capsicmn annuum* L.

Experimental Example 1-3: Chimeric Parameter Setting and Testing

Figure 3:
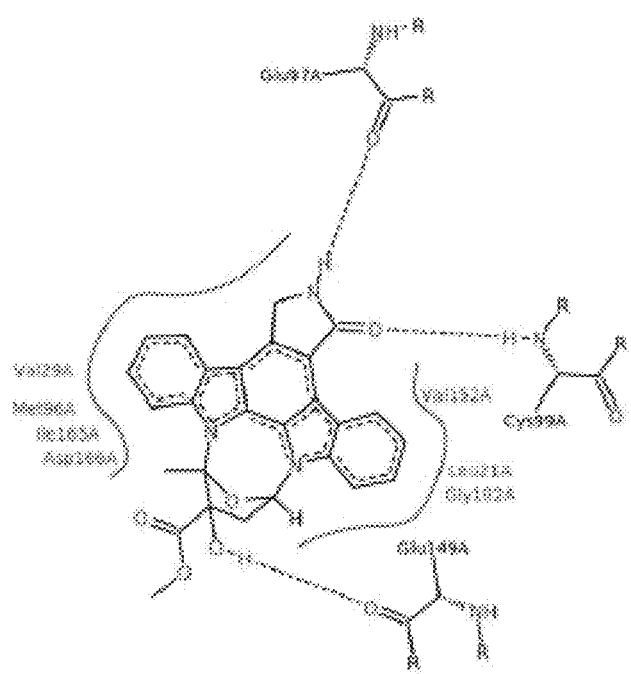
FIG. 3 is a schematic view illustrating binding of the inhibition KSA and NF-kB protein 25 according to the preferred embodiment of the present invention.

The crystal structure of NF-κB protein is the same as that published in Journal of Biological Chemistry, 2013 and a code of the crystal structure in Protein Data Bank is 4KIK, a resolution is 2.83 Å. NF-κB is a Trimer structure having an inhibition KSA. FIG. 3 is a schematic view illustrating binding of the inhibition KSA and NF-kB protein so as to disclose information of amino acids of NF-κB inhibition zone.

Figure 4:
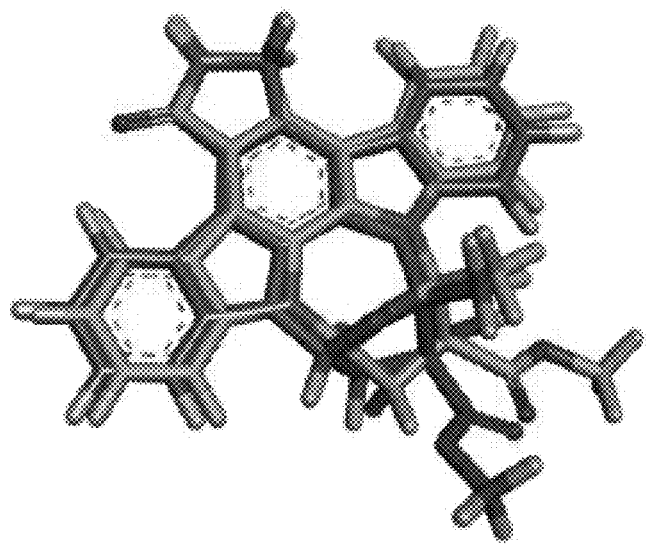
FIG. 4 is a schematic view illustrating stacking result of the decrystallization structure and the intercalation structure (indicated by green color) according to the preferred embodiment of the present invention.
Figure 5:
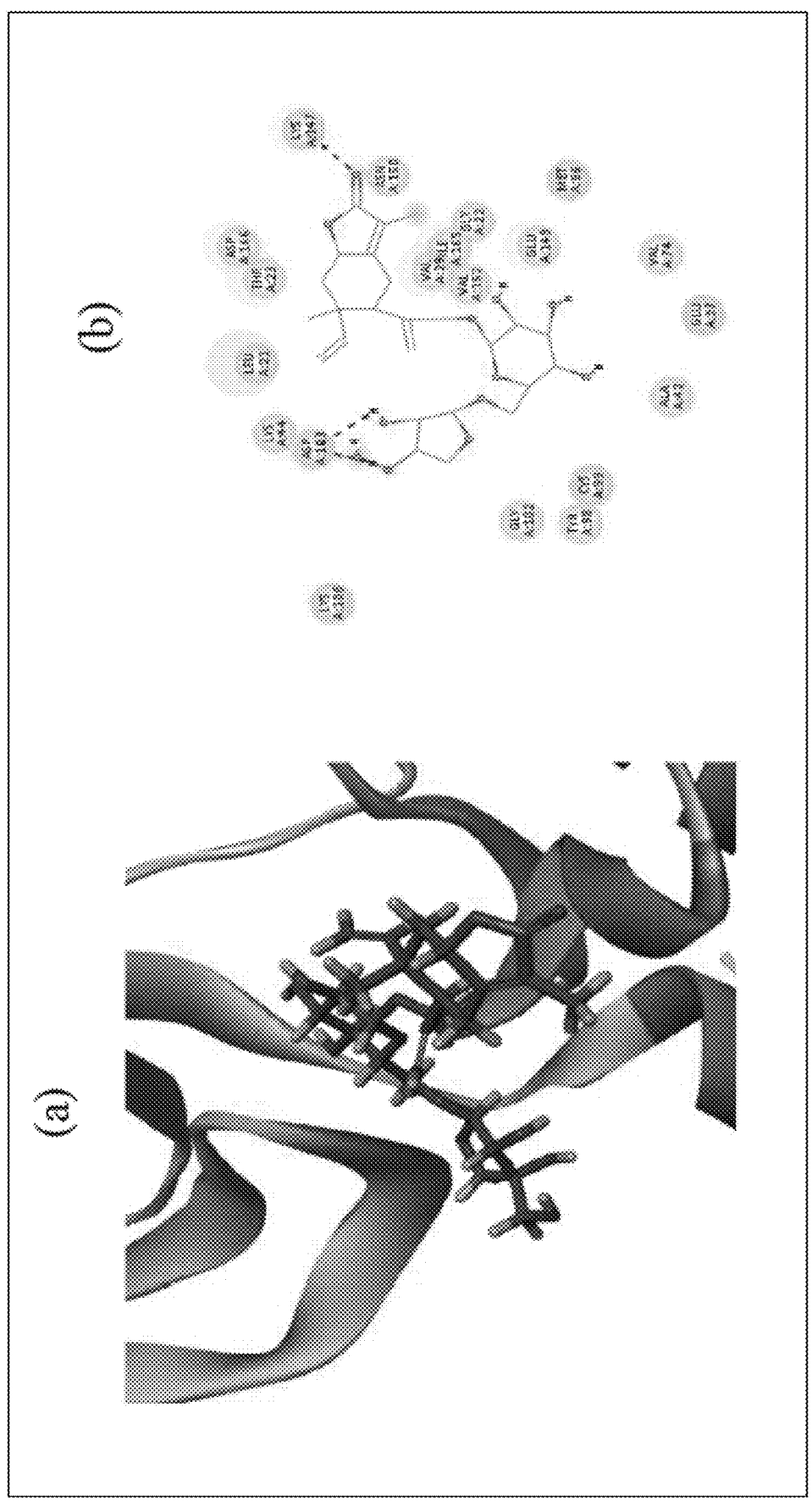
FIGS. 5a-5b are schematic views respectively illustrating three-dimensional state and two-dimensional state of intercalate of the formula (1) of the phytochemicals and NF-κB protein according to the preferred embodiment of the present invention.
Figure 6:
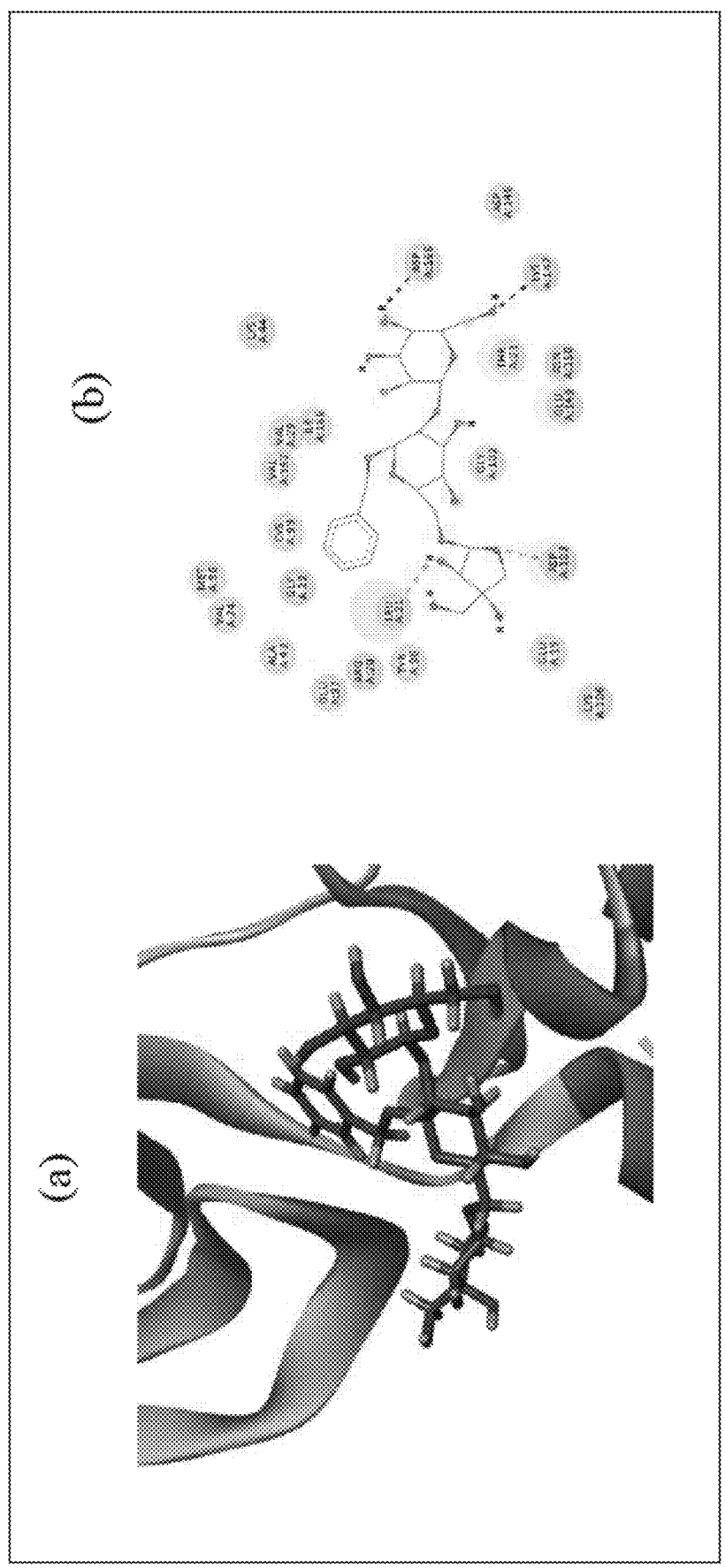
FIGS. 6a-6b are schematic views respectively illustrating three-dimensional state and two-dimensional state of intercalate of the formula (2) of the phytochemicals and NF-κB protein according to the preferred embodiment of the present invention.
Figure 7:
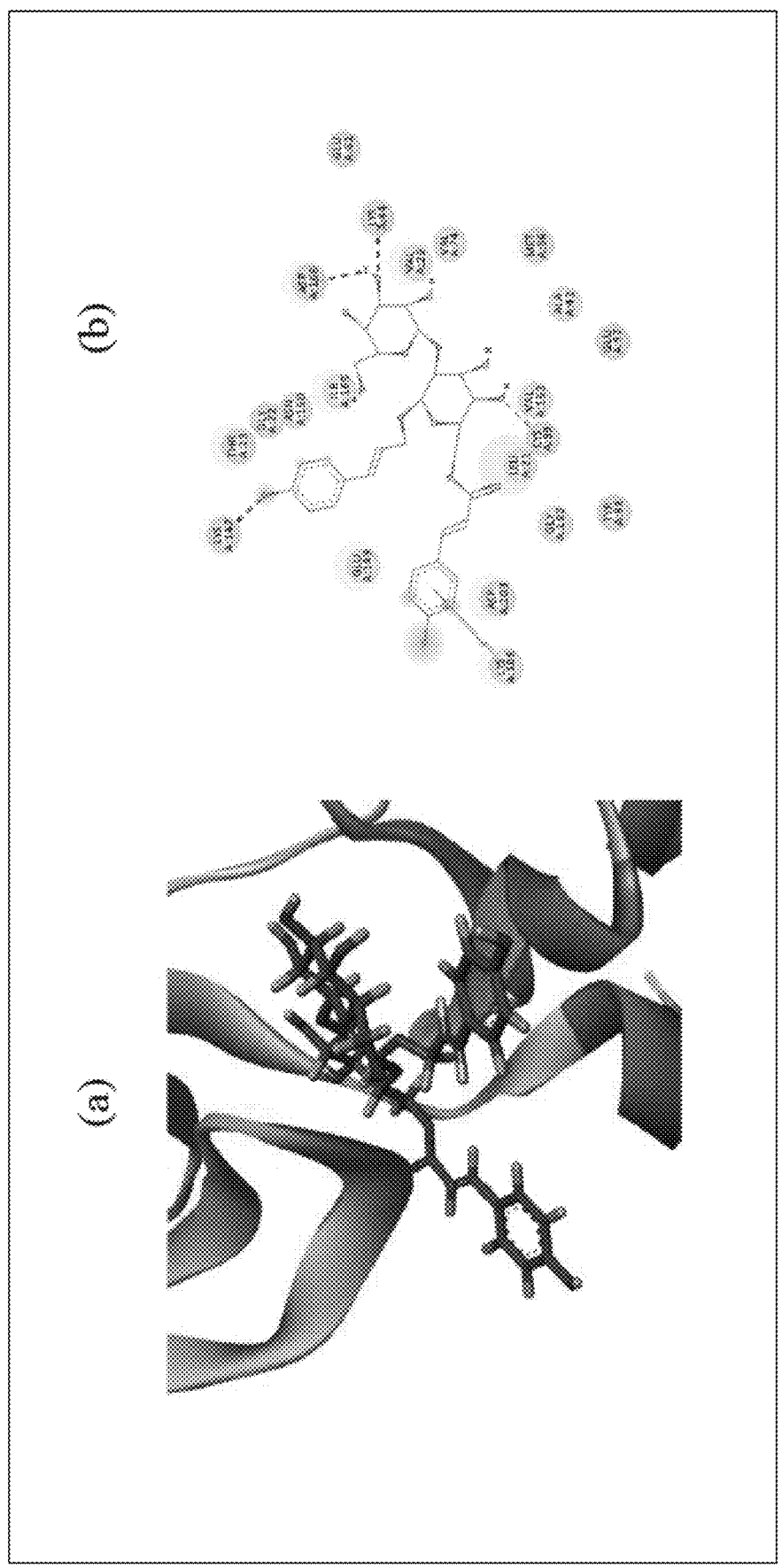
FIGS. 7a-7b are schematic views respectively illustrating three-dimensional state and two-dimensional state of intercalate of the formula (3) of the phytochemicals and NF-κB protein according to the preferred embodiment of the present invention.
Figure 8:
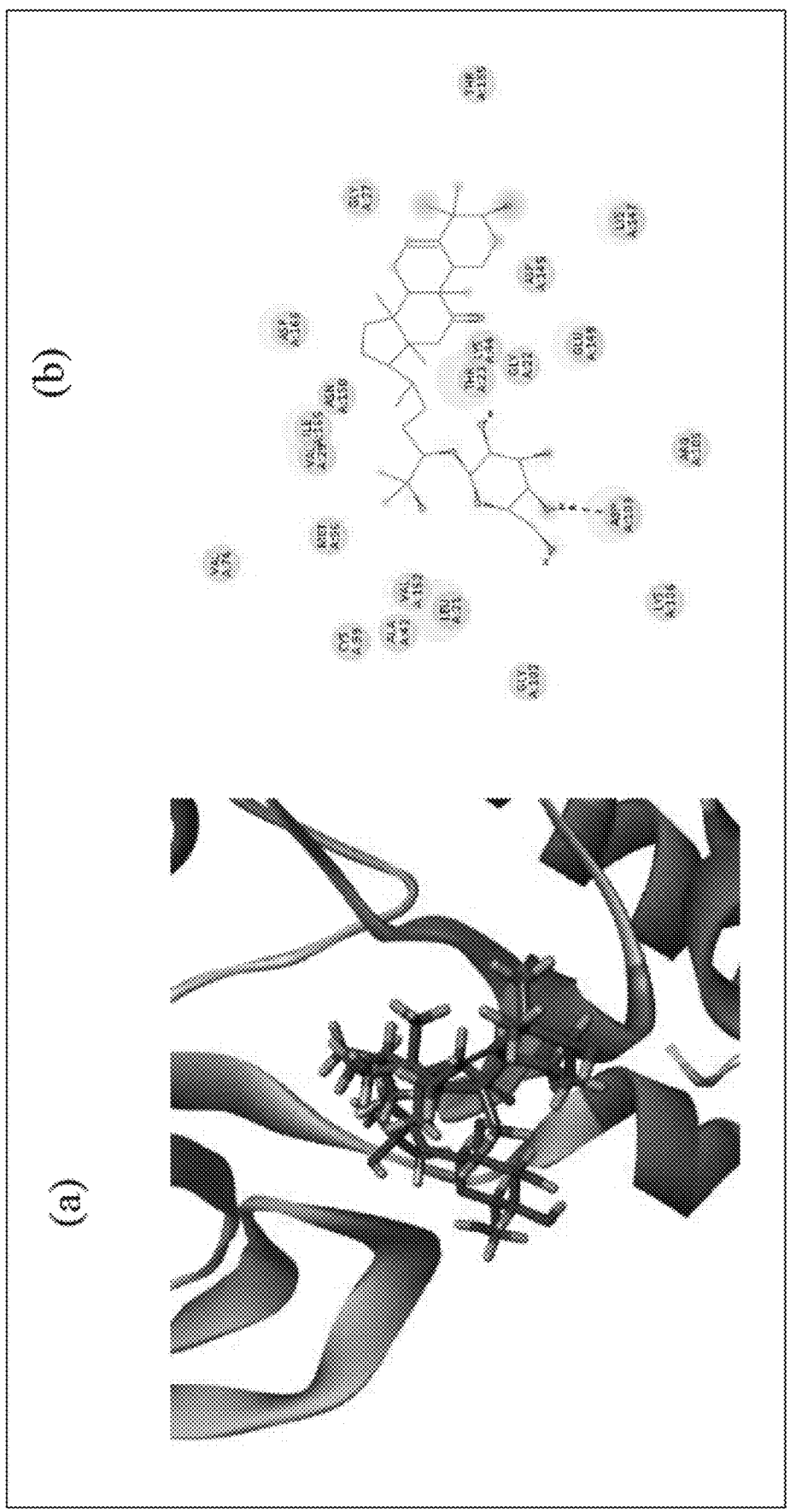
FIGS. 8a-8b are schematic views respectively illustrating three-dimensional state and two-dimensional state of intercalate of the formula (4) of the phytochemicals and NF-κB protein according to the preferred embodiment of the present invention.
Figure 9:
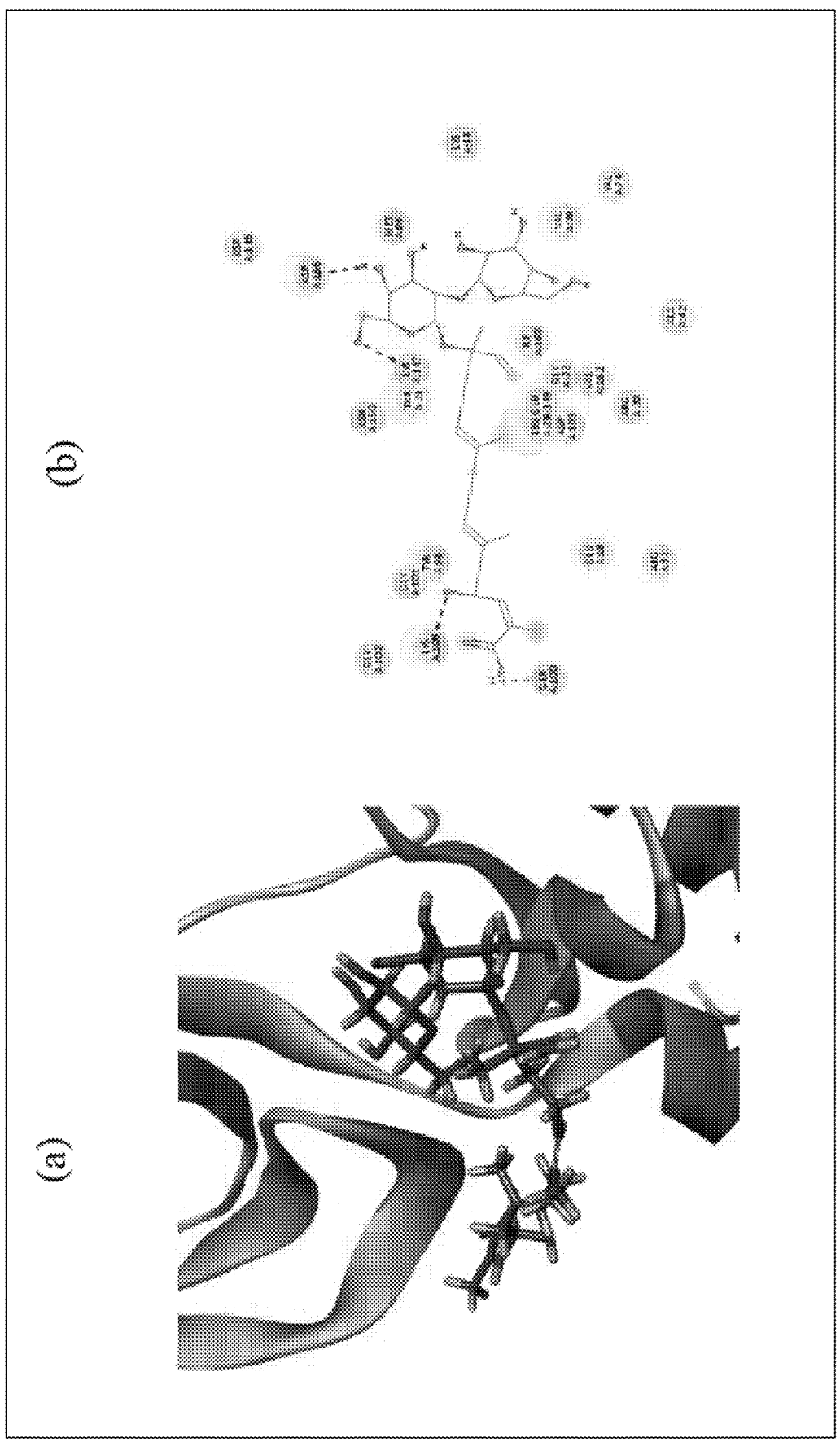
FIGS. 9a-9b are schematic views respectively illustrating three-dimensional state and two-dimensional state of intercalate of the formula (5) of the phytochemicals and NF-κB protein according to the preferred embodiment of the present invention.

A binding structure of the NF-kB protein and the phytochemicals is forecasted by way of CHARMm-based molecular dynamics docking. Intercalate parameters are find out by using the inhibition KSA, and the three-dimensional configuration of the binding structure is almost identical to an actual decrystallization structure so that phytochemicals intercalate to the NF-kB protein. FIG. 4 is a schematic view illustrating stacking result of the decrystallization structure and the intercalation structure (indicated by green color), wherein the root-mean-square deviation (RMSD) is 0, and compounds, intercalating into the NF-kB protein, effectively simulate decrystallization state by using the intercalate parameters.

FIGS. 5a-9b are schematic views respectively illustrating three-dimensional state and two-dimensional state of intercalate of the formula (1), the formula (2), the formula (3), the formula (4), and the formula (5) of the phytochemicals.

As shown in FIGS. FIGS. 5a-9b, when the formula (1), the formula (2), the formula (3), the formula (4), and the formula (5) intercalate into the NF-kB protein and the amino acids, they meet with a size of the NF-κB inhibition zone so as to enhance immune regulation and anti-inflammatory by way of the NF-kB protein.

Experimental Example 2-1: Extraction of Plant Compounds

The Compound (A) refer to formula (1) was designed by computer-assisted drug design. After comparison with the database, suitable plants were obtained for extraction to measure the activity:

Compound (A)

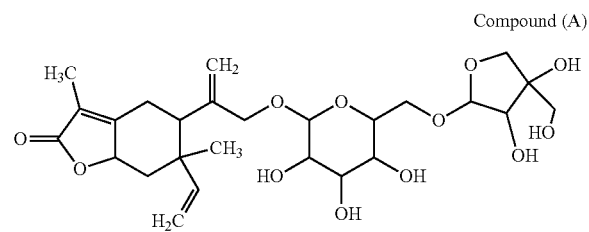 [SMILES: C=CC1(C)CC2OC(=O)C(C)=C2CC1C(=C)COC1OC(COC2OCC(O)(CO)C2O)C(O)C(O)C1O]

In accordance with the result of the database search, the plant compound source may be strawberry, and the strawberry variety may include but is not limited to *Fragaria* x *ananas, Fragaria havatai* Makino, *Fragaria chiloensis, Fragaria nilgerrensis, Fragaria nipponica, Fragaria nilgerrensis* Schlecht., *Fragaria virginiana, Fragaria* x *vesca* or *Fragaria Iturupensis* Staudt. Compound (A) belongs to a terpenoid (Terpenes).

According to the study by Kim et al. (2013), volatile steroids contained in strawberries include monoterpenoids, sesquiterpenoids, dipterens, and triterpenes. Terpenes are widely found in various parts of strawberry plants, especially roots, stems, leaves, calyx and other green parts of the strawberry plant.

For example, the strawberry variety *Fragaria* x *ananass* was chosen as a plant sample. The whole plant of strawberry was extracted with different solvents, and the extraction rate was calculated. 95% ethanol was selected as the optimum solvent, and water extraction was used as the control group. 95% ethanol was heated to extract the sample using a hot reflux extraction apparatus, and heating was calculated from boiling for 3 hours, and the heating vessel was taken out and allowed to cool. After standing and letting cool, use a sieve to initially filter the sample waste residue. The sample was then filtered through a Buchner funnel and the filtered liquid was properly stored at 4° C. until concentration. Concentration was carried out using a vacuum concentration system (sample heating temperature 53-56° C. in vacuum environment), and then all the concentrated thick liquids were uniformly mixed, vacuum freeze-dried and the dried samples were collected.

Experimental Example 2-2: Cell Test of Anti-Inflammatory of Strawberry Plant Extract (1)

Since the compound (A) belongs to a terpenoid, it may play a special flavor role in the ripening process of the strawberry. It is known that if the fruit ripens under different environments may induce the gene expression of the plant compound to produce different flavors and appearance. Therefore, we exert different temperatures and photoperiod as experimental conditions between the anthesis stage and the first harvest stage to observe the relationship between environmental factors of the strawberry ripening process and the anti-inflammatory effect of immune cells of strawberry plant extracts.

In the present specification, the term "strawberry plants" is meaning "the whole plant of strawberry" which the total of strawberry roots, stems, calyx and leaves accounts for about 60%-95%, and the strawberry fruits account for about 5%-40%. The term "anthesis stage" refers to the period from the beginning of the flowering period to the time when the flower is completely open and functional; the term "first harvest stage" refers to the beginning of the growth of the fruit to the initial stage of the fully ripe strawberry.

The sample is treated between the anthesis stage and the first harvest stage to enhance terpenoid gene expression. The samples were incubated for 4-7 days at 25° C. and 15° C. environment respectively, and natural photoperiod (16/8, Natural light) and darkly incubation conditions respectively. Finally, the plants were harvested and subjected to 95% ethanol/water extraction. The term "darkly incubation" in the embodiments of the present invention means that the sample plants are placed in a dark room or completely covered with an opaque article for 24 hours without interruption.

95% ethanol-extracted strawberry plant extract (SBE) was pre-tested at a concentration of 50 μg/ml, with peripheral macrophage cell line RAW264.7, lung macrophage cell line MHS and neuromacromocyte cell line BV2 were tested by LPS stimulation mode. LPS induces the release of NO, and the cell culture medium is subjected to NO (nitrite/nitrate) yield analysis.

Figure 10:
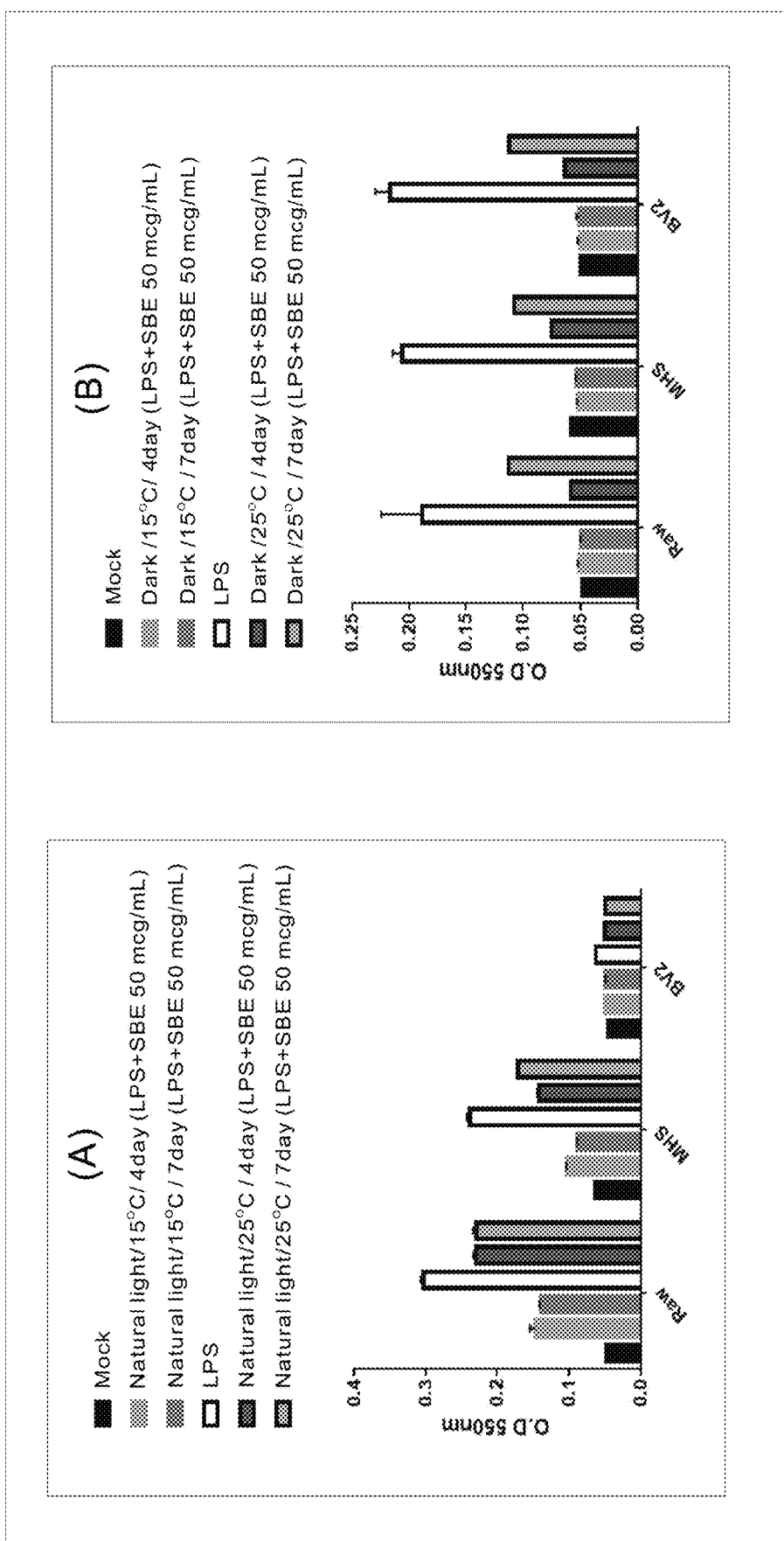
FIG. 10 (A), (B) are the results of anti-inflammatory tests of strawberry plant extracts (SBE) under different fruit ripening conditions of the present invention.

FIG. 10 (A), (B) are the results of anti-inflammatory tests of strawberry plant extracts (SBE) under different fruit ripening conditions of the present invention. FIG. 10 (A) is the anti-inflammatory test results of the cells of the strawberry plant extract (SBE) harvested from plants after 4 or 7 days incubation under natural light cycle (16/8, Natural light) at 25° C. and 15° C.; FIG. 10 (B) is the anti-inflammatory test results of the cells of the strawberry plant extract (SBE) harvested after 4 or 7 days of incubation in a dark room at 25° C. and 15° C.

As shown in FIGS. 10 (A) and (B), the strawberry plant extract (SBE) of the plant was harvested after treatment for 4 or 7 days in a dark room at 25° C. and 15° C. Its anti-inflammatory effect is significantly better than the plants harvested after 4 or 7 days under natural light cycle (16/8, Natural light) at 25° C. and 15° C.

Therefore, the dark incubation is a benefit for obtaining strawberry plants extract (SBE) having better anti-inflammatory efficiency. In addition, the strawberry fruits ripened in the dark are exhibit a green-white, white or white-red color. According to an embodiment of the present invention, the temperature of darkly incubation is between 15° C. to 25° C., in a further embodiment of the present invention, the darkly incubation with a lower temperature (15° C. or lower), may promote the anti-inflammatory effect of strawberry plant extract (SBE).

Experimental Example 2-3: Cell Test of Anti-Inflammatory of Strawberry Plant Extract (2)

According to the above, the strawberry plants were treated in a dark room at 15° C. for 4-7 days, ensure the strawberry fruits have exhibited a green-white, white or white-red colors for the harvesting standard. Then the whole plants were harvested for further extraction. 95% ethanol (95% EtOH) was used as the experimental group, and water (H2O) was used as the control group. Three dose groups are divided as 10 ug/ml, 50 ug/ml, 100 ug/ml of 95% ethanol extracted Strawberry plant extracts (SBE) were used to treat the mouse peripheral macrophage cell line RAW264.7, lung macrophage cell line MHS and neuromacromocyte cell line BV2, respectively. In contrast group, three dose groups are divided as 10 ug/ml, 50 ug/ml, 100 ug/ml of water extracted strawberry plant extracts (SBE) were used to treat cells, respectively.

Figure 11:
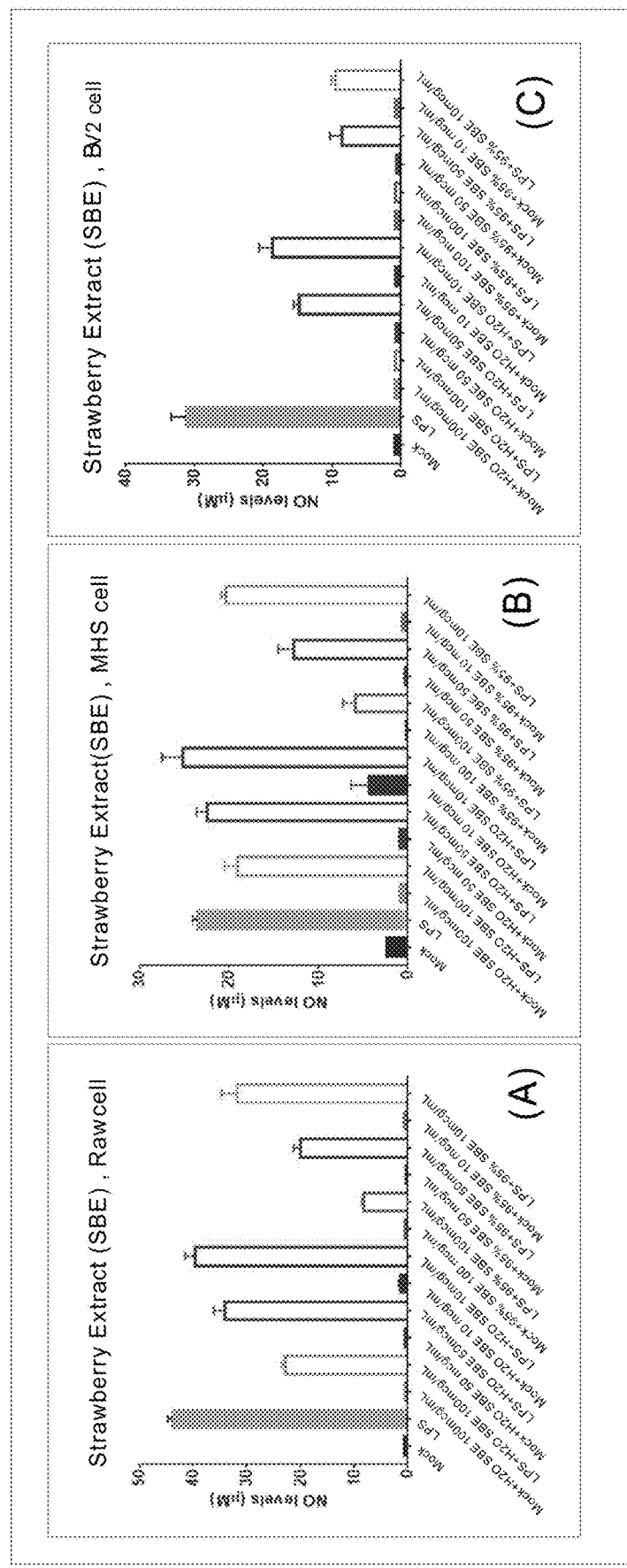
FIGS. 11 (A), (B) and (C) are the results of anti-inflammatory tests of strawberry plant extracts (SBE) under different extraction conditions of the present invention.

FIG. 11 is the results of anti-inflammatory tests of strawberry plant extracts (SBE) under different extraction conditions of the present invention. FIG. 11(A) shows the results of the LPS stimulation mode in cell line RAW264.7; FIG. 11(B) shows the results of the LPS stimulation mode in cell line MHS; and FIG. 11(C) shows the results of the LPS stimulation mode in cell line BV21.

As shown in FIG. 11(A), exhibits a dose-dependent result in the cell line RAW264.7 by treated with a concentration of 50, and 100 ug/ml of 95% ethanol extracted SBE. The result shows that the 95% ethanol extract SBE has the effect of reducing the expression of NO by LPS. In contrast, except for the high dose group (100 ug/ml), water extracted SBE was not very effective to reduce the expression of NO.

FIG. 11(B) present a dose-dependent trend in the cell line MHS treated with 95% ethanol extract SBE at a concentration of 10, 50, 100 ug/ml. The result shows that the 95% ethanol extract SBE has the effect of reducing the expression of NO secretion stimulated by LPS. The contrast group was not very effective.

Referring to FIG. 11 (C), cell line BV2 was treated with a 95% ethanol extracted SBE at a concentration of 10, 50, 100 ug/ml, which significantly reduced the performance of LPS-stimulated NO secretion in a dose-dependent trend. The 10, 50 and 100 ug/ml of water extracted SBE also showed the effect of inhibiting the secretion of inflammatory mediators in the cell line BV2.

Therefore, using the 95% ethanol as an extraction solvent is beneficial to obtain strawberry plants extract (SBE) having better anti-inflammatory efficiency.

Figure 12:
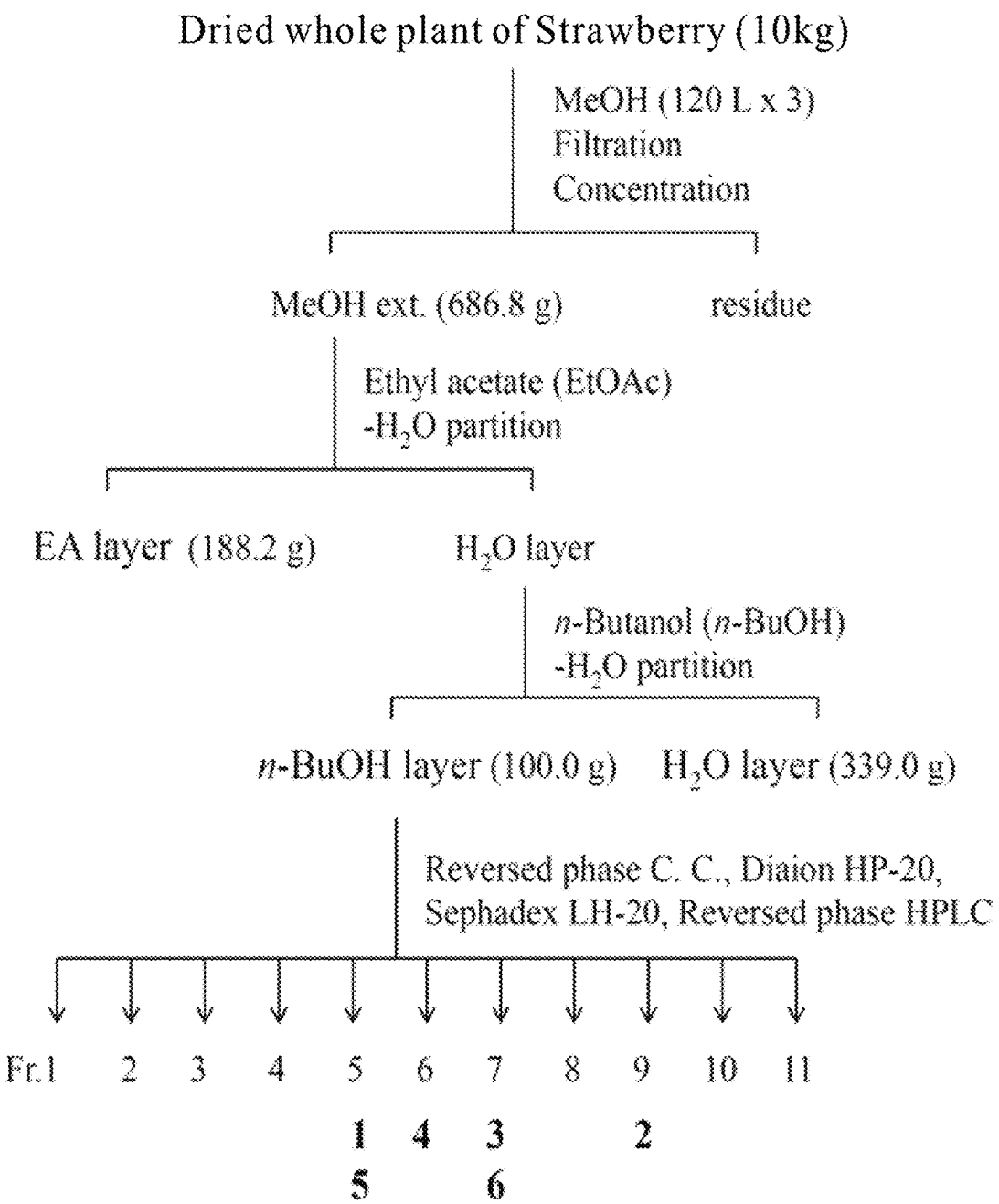
FIG. 12 is a flow chart showing the separation of strawberry plant extracts.

Experimental Example 3: Purification and Quantitative Analysis of Active Components of Strawberry Plant Extracts FIG. 12 is a flow chart for the separation of strawberry plant extracts. The ethanol extract of the strawberry plants was separated into an ethyl acetate layer, an n-butanol layer and an aqueous layer using a partition extraction separation method.

Figure 13:
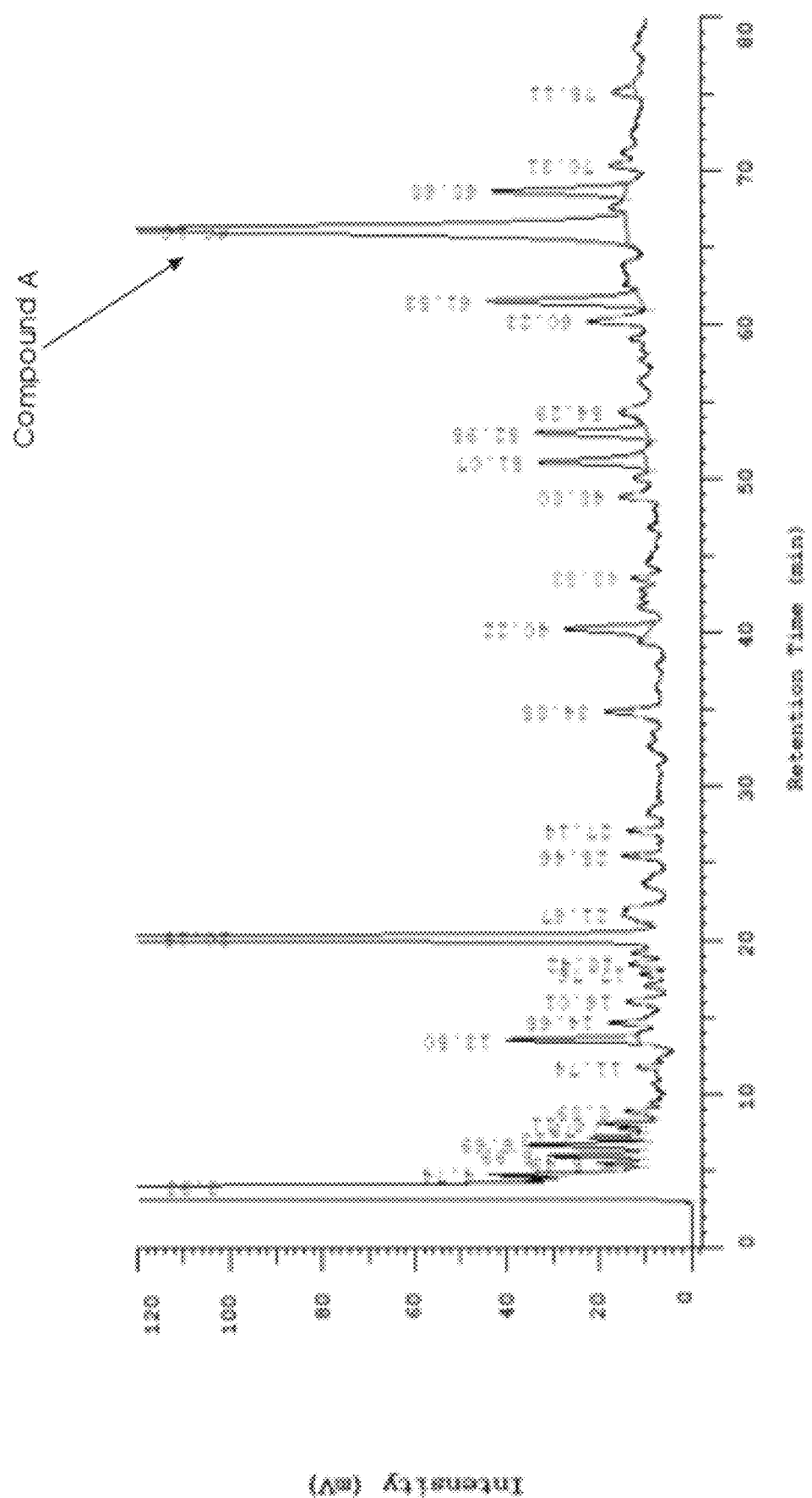
FIG. 13 is a result of HPLC analysis of n-butanol layer extract of strawberry plant extract.

FIG. 13 is a result of HPLC analysis of n-butanol layer extract of strawberry plant extract (SBE).

Sample preparation: Take 10 mg of SBE n-butanol layer extract; add 1 ml of dimethyl hydrazine (DMSO); filter with a 0.45 μm syringe filter; and chill at 4° C. The component analysis and structural identification of Compound (1) was processed by further high-performance liquid chromatography (HPLC). Chromatography was performed by using a C-18 liquid chromatography column (Phenomenex Luna C-18 column), the mobile phase (Mobile phase) was Water/Acetonitrile=0 min: 93/7, 3 min: 93/7, 70 min: 83/17, 75 min: 38/17), flow rate was 1 ml/min, and HPLC-UV detection wavelength was 227 nm. The structure of the compound (A) was identified as shown in Table 1 below. Powder; 1H-NMR (400 MHz, CD3OD) and 13C-NMR (100 MHz, CD3OD).

TABLE 1 structure identification of Compound (A)

| | Sample 6 | |
|---|---|---|
| Position | $\delta H$ | $\delta C$ |
| 1 | 5.81dd (17.6, 10.8) | 148.0 d |
| 2 | 4.98 d (11.2) | 112.6 t |
|   | 4.99 d (11.2) | |
| 3 | 5.05br · s | 115.5 t |
|   | 5.39br · s | |
| 4 | | 147.1 s |
| 5 | 2.30dd (13.6, 4.0) | 48.3 d |
| 6 | 2.82dd (13.6, 4.0) | 29.2 t |
|   | 2.70 t (12.8) | |
| 7 | | 165.4 s |
| 8 | | 79.7 d |
| 9 | 1.34 t (12.0) | 46.9 t |
|   | 2.13dd (12.0, 6.0) | |
| 10 | | 41.9 s |
| 11 | | 120.5 s |
| 12 | | 177.3 s |
| 13 | 1.79 s | 8.1 q |
| 14 | 1.19 s | 16.6 q |
| 15 | 4.07d (13.2) | 74.9 t |
|   | 4.23 d (13.2) | |
| 1' | 4.22 d (8.0) | 104.4 d |
| 2' | 3.18 t (8.8) | 75.0 d |
| 3' | 3.34 d (8.0) | 78.0 d |
| 4' | 3.24 t (8.8) | 71.7 d |
| 5' | 3.37 m | 77.9 d |
| 6' | 3.58dd (11.2, 9.2) | 68.7 t |
|   | 3.96dd (9.2, 2.4) | |
| Api-1 | 4.99 d (2.4) | 110.9 d |
| Api-2 | 3.88 d (2.4) | 78.0 d |
| Api-3 | | 80.5 s |
| Api-4 | 3.75 d (9.6) | 74.8 t |
|   | 3.95 d (9.6) | |
| Api-5 | 3.55 br · s | 65.4 t |

According to the above, the Compound (A) can be purified from the 95% ethanol extracted SBE. In accordance with the embodiment of the present invention, the Compound (A) is chimeric in the NF-κB protein to interact with the amino acid of the NF-κB protein inhibitory region which can achieve the effect of enhancing immunomodulation and/or anti-inflammatory activity by inhibiting NF-κB protein activity.

According to one embodiment of the invention, a strawberry plant extract can be combined with an optional edible carrier to form a composition. The composition may be in the form of a beverage, a lozenge, a pill, a capsule, a granule, a powder, a suspension, a sachet, a pastille, a candy, a stick or a syrup.

According to another embodiment of the present invention, the above plant compounds and compositions are useful for the preparation of a pharmaceutical product, food or nutritional supplement that enhances immuno-modulatory and/or anti-inflammatory activity. The nutritional supplement of the present invention includes food supplements and functional foods. "Food supplement" means a product made from a compound used in a normal food, but it is a tablet, powder, capsule, medicament or any other form which is generally not associated with nourishment and which has a beneficial effect on human health. "Functional foods" are nourishment products, and they also have beneficial effects on human health.

The composition according to the invention is a dietary supplement which can be mixed with a suitable drinkable liquid, such as water, yoghurt, milk or juice, or can be mixed with a solid or liquid food. The form of the dietary supplement may be a tablet, a pill, a capsule, a lozenge, a granule, a powder, a suspension, a sachet, a pasty; a candy, a stick, a syrup, and a corresponding administration form, usually the form of the unit dose. Preferably, the dietary supplement comprising the composition of the invention is administered in the form of a lozenge, lozenge, capsule or powder for the manufacture of a dietary supplement.

The one or more plant compounds described above may be combined with an optional edible carrier to form a composition. The composition may be in the form of a beverage, a lozenge, a pill, a capsule, a granule, a powder, a suspension, a sachet, a pastille, a candy, a stick or a syrup. And further using the above plant compound or composition thereof for the preparation of a pharmaceutical product, food or nutritional supplement that enhances immunomodulatory and/or anti-inflammatory activity While the embodiments of the invention have been set forth for the purpose of disclosure, modifications of the disclosed embodiments of the invention as well as other embodiments thereof may occur to those skilled in the art. The scope of the claims should not be limited by the embodiments set forth in the examples, but should be given the broadest interpretation consistent with the description as a whole.

What is claimed is:

1. A method for preparing a strawberry plant extract, comprising:
   a darkly incubation of a strawberry plant between an anthesis stage and a first harvest stage;
   harvesting the strawberry plant in a green-white, white or white-red color of the strawberry fruit; and
   extracting the strawberry plant with ethanol to obtain a strawberry plant extract, wherein the strawberry plant comprises:
      60% to 95% of an add up of strawberry roots, stems, leaves, and calyxes; and
      5% to 40% of the strawberry fruit.

2. The method according to claim 1, wherein the darkly incubation is carried out for 4 to 7 days between a period of the anthesis stage and first harvest stage.

3. The method according to claim 1, wherein the ethanol is 95% ethanol.

4. The method according to claim 1, wherein the strawberry plant is selected from the group consisting of *Fragaria* x *ananass*, *Fragaria hayatai* Makino, *Fragaria chiloensis*, *Fragaria nilgerrensis*, *Fragaria nipponica*, *Fragaria nilgerrensis* Schlecht., *Fragaria virginiana*, *Fragaria* x *vesca*, *Fragaria iturupensis* Staudt, and any combination thereof.

5. The method according to claim 1, wherein the strawberry plant extract comprises a Compound (A) which is available to bind to a region of inhibition of NF-KB:

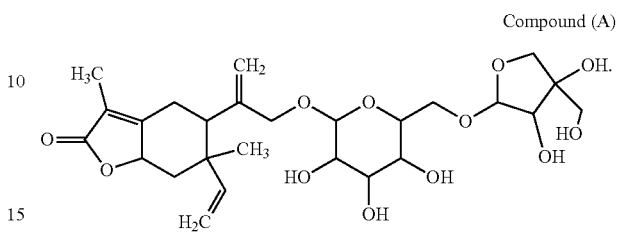

Compound (A)

6. The method according to claim 1, further comprising performing the darkly incubation at a temperature of 15° C.

7. The method according to claim 6, wherein the darkly incubation is carried out for 4 to 7 days between a period of the anthesis stage and first harvest stage.

8. The method according to claim 6, wherein the ethanol is 95% ethanol.

9. The method according to claim 6, wherein the strawberry plant is selected from the group consisting of *Fragaria* x *ananass*, *Fragaria hayatai* Makino, *Fragaria chiloensis*, *Fragaria nilgerrensis*, *Fragaria nipponica*, *Fragaria nilgerrensis* Schlecht., *Fragaria virginiana*, *Fragaria* x *vesca*, *Fragaria iturupensis* Staudt, and any combination thereof.

10. The method according to claim 6, wherein the strawberry plant extract comprises a Compound (A) which is available to bind to a region of inhibition of NF-κB:

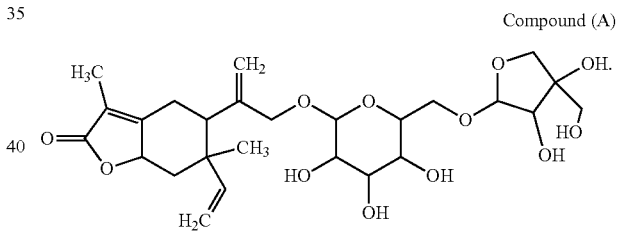

Compound (A)

* * * * *